United States Patent
Glenwright et al.

(10) Patent No.: US 7,163,606 B2
(45) Date of Patent: Jan. 16, 2007

(54) PROCESS FOR RECOVERING METHYLENE CHLORIDE

(75) Inventors: Thomas B. Glenwright, Webster, NY (US); Warren R. Smith, Webster, NY (US); Betsy B. Dodge, Williamson, NY (US); Steven P. Wazenkewitz, Sodus, NY (US); Ronald L. Swift, Duvall, WA (US)

(73) Assignee: Xerox Corporation, Stamford, CT (US)

( * ) Notice: Subject to any disclaimer, the term of this patent is extended or adjusted under 35 U.S.C. 154(b) by 287 days.

(21) Appl. No.: 10/744,792

(22) Filed: Dec. 23, 2003

(65) Prior Publication Data

US 2005/0133359 A1  Jun. 23, 2005

(51) Int. Cl.
*B01D 3/42* (2006.01)
*C07C 17/383* (2006.01)

(52) U.S. Cl. ............................. 203/2; 203/14; 570/262

(58) Field of Classification Search .................... 203/2, 203/14, DIG. 18, DIG. 9; 202/160; 570/211, 570/262

See application file for complete search history.

(56) References Cited

U.S. PATENT DOCUMENTS

| | | | | |
|---|---|---|---|---|
| 4,204,913 A | * | 5/1980 | Sabatka | 202/168 |
| 5,248,393 A | * | 9/1993 | Schumacher et al. | 202/158 |
| 5,980,695 A | * | 11/1999 | Cox et al. | 202/166 |
| 6,551,465 B1 | * | 4/2003 | Van Zile et al. | 202/158 |
| 6,638,397 B1 | * | 10/2003 | Camiener et al. | 202/161 |
| 6,911,120 B1 | * | 6/2005 | Young | 203/2 |
| 6,945,536 B1 | * | 9/2005 | Iwakata et al. | 277/552 |

* cited by examiner

*Primary Examiner*—Virginia Manoharan
(74) *Attorney, Agent, or Firm*—Eugene O. Palazzo; Fay, Sharpe, Fagan, Minnich & McKee, LLP

(57) ABSTRACT

A system for recovering methylene chloride from an aqueous waste stream is disclosed. The system includes a distillation unit, at least one heat transfer unit, receptacles for methylene chloride and waste product, a temperature probe and a controller configured to selectively divert product flow from the distillation unit to either of the receptacles or to a recycle line back to the distillation unit depending upon the temperature measured by the probe. Also disclosed is a related process of recovering methylene chloride with such a system.

3 Claims, 1 Drawing Sheet

PROCESS FOR RECOVERING METHYLENE CHLORIDE

BACKGROUND

There is disclosed herein a process for recovering methylene chloride from an aqueous water solution and the recovered methylene chlorine produced thereby. More particularly, the exemplary embodiment disclosed herein relates to the use of a recycle stream in a batch distillation process for recovering methylene chloride from a waste stream. The process reduces hazardous waste and improves the reclaim efficiency of methylene chloride. The exemplary embodiment finds particular application in conjunction with recovering methylene chloride used as a solvent in photoreceptor fabrication, and will be described with particular reference thereto. However, it is to be appreciated that the present exemplary embodiment is also amenable to other like applications.

Photoreceptor fabrication requires reagent grade (i.e., 99.99% purity) methylene chloride which is used as a solvent. Typically, a recycling system captures the solvent as it vaporizes in a carbon bed. The captured solvent is removed from the carbon bed with steam and the resulting water/methylene chloride mixture is distilled to recover the solvent. Previous operations monitored the distillation process and diverted the recovered solvent once the quality or concentration level of the solvent fell below reagent grade. This technical grade material can be sold to entities who market it as paint remover, etc. However, this practice requires that the methylene chloride solvent is frequently replenished during the photoreceptor fabrication process. Furthermore, another disadvantage of this practice is that the low quality solvent shipped to other entities be designated as hazardous waste.

The present exemplary embodiment contemplates a new and improved process for recovering methylene chloride which overcomes the above-referenced problems and others.

BRIEF DESCRIPTION

The present exemplary embodiment provides, in one aspect, a system for recovering methylene chloride from an aqueous waste stream. The system comprises a distillation unit having an inlet adapted to receive an aqueous waste feed stream containing methylene chloride. The distillation unit is also adapted to produce a product stream at an outlet of the distillation unit. The system also comprises at least one heat transfer unit in communication with the product stream and adapted to transfer thermal energy from the product stream. The heat transfer unit has an inlet and an outlet for the product stream. The inlet of the heat transfer unit is in communication with the product stream of the distillation unit. The system also comprises a methylene chloride receptacle having a first selectively controllable inlet valve. The system also comprises a waste receptacle having a second selectively controllable inlet valve. The system further comprises a recycle flow line having a third selectively controllable inlet valve. The recycle line is in communication with the feed stream. Each of the methylene chloride receptacle, waste receptacle, and recycle flow line is in selective communication with the outlet of the heat transfer unit for receiving the product stream. The system additionally comprises a first temperature sensor adapted to measure the temperature of the product stream exiting the distillation unit and a second temperature sensor adapted to measure the temperature at the bottom of the distillation unit. A controller is also provided in communication with the first and second temperature sensors, the first selectively controllable inlet valve, the second selectively controllable inlet valve, and the third selectively controllable inlet valve. Upon the temperature sensors sensing the product stream and bottom portion of the distillation unit having particular temperatures, the controller independently actuates each of the first, second, and third inlet valves to selectively divert the product stream.

The exemplary embodiment also provides, in another aspect, a system for reclaiming methylene chloride from a mixture including methylene chloride and water. The system comprises a distillation unit having an inlet for receiving the mixture and an outlet for a product exiting the unit. The system also comprises a plurality of control valves having an inlet and at least a first, a second, and a third outlet. The inlet of the valves is in communication with the outlet of the distillation unit. The valves are adapted to divert flow from the inlet to one of the first, second, or third outlets upon actuation. The system also comprises a flow line providing communication between the third outlet and the inlet of the distillation unit. A plurality of temperature sensors are also provided. The temperature sensors are adapted to measure the temperature of the product exiting the distillation unit and the temperature of a lower region of the distillation unit to provide at least one output signal indicative of the measured temperature. The system further comprises a controller adapted to receive the output signal from the temperature sensors and actuate the control valves. Upon the temperature sensors measuring a particular temperature of the product exiting the distillation unit and a certain temperature of the lower region of the distillation unit, the controller actuates the control valves to divert flow from the inlet of the control valves to one of the first, second, or third outlets of the valves.

The exemplary embodiment, in yet another aspect, also provides a process for recovering methylene chloride from a mixture including water and methylene chloride. The process comprises providing a system including (i) a distillation unit having an inlet and an outlet, (ii) a plurality of selectively positionable control valves each having an inlet and an outlet, one of the outlets being in communication with the inlet of the distillation unit, (iii) a plurality of temperature sensors and means for providing a control signal corresponding to sensed temperatures, and (iv) a controller in communication with the temperature sensors and the control valves. The process also comprises directing the mixture including water and methylene chloride to the inlet of the distillation unit. The process further comprises operating the distillation unit to produce a product stream at the outlet of the distillation unit. The process additionally comprises measuring the temperature of the product stream and a temperature at a lower region of the distillation unit with the temperature sensors. The process further comprises providing the control signal from the temperature sensors to the controller. The process also comprises operating the controller to selectively position the control valves based upon the control signal.

One advantage of the present exemplary embodiment is the provision of improved recovery of methylene chloride from an aqueous waste stream.

Another advantage of the present exemplary embodiment is that the amount of hazardous waste in the form of a stream of methylene chloride and water, is reduced.

Still further advantages and benefits of the present exemplary embodiment will become apparent to those of ordinary skill in the art upon reading and understanding the following detailed description of the preferred embodiments.

BRIEF DESCRIPTION OF THE DRAWINGS

The exemplary embodiment may take form in various components and arrangements of components, and in various steps and arrangements of steps. The drawings are only for purposes of illustrating preferred embodiments and are not to be construed as limiting the exemplary embodiment.

DETAILED DESCRIPTION

Figure 1:
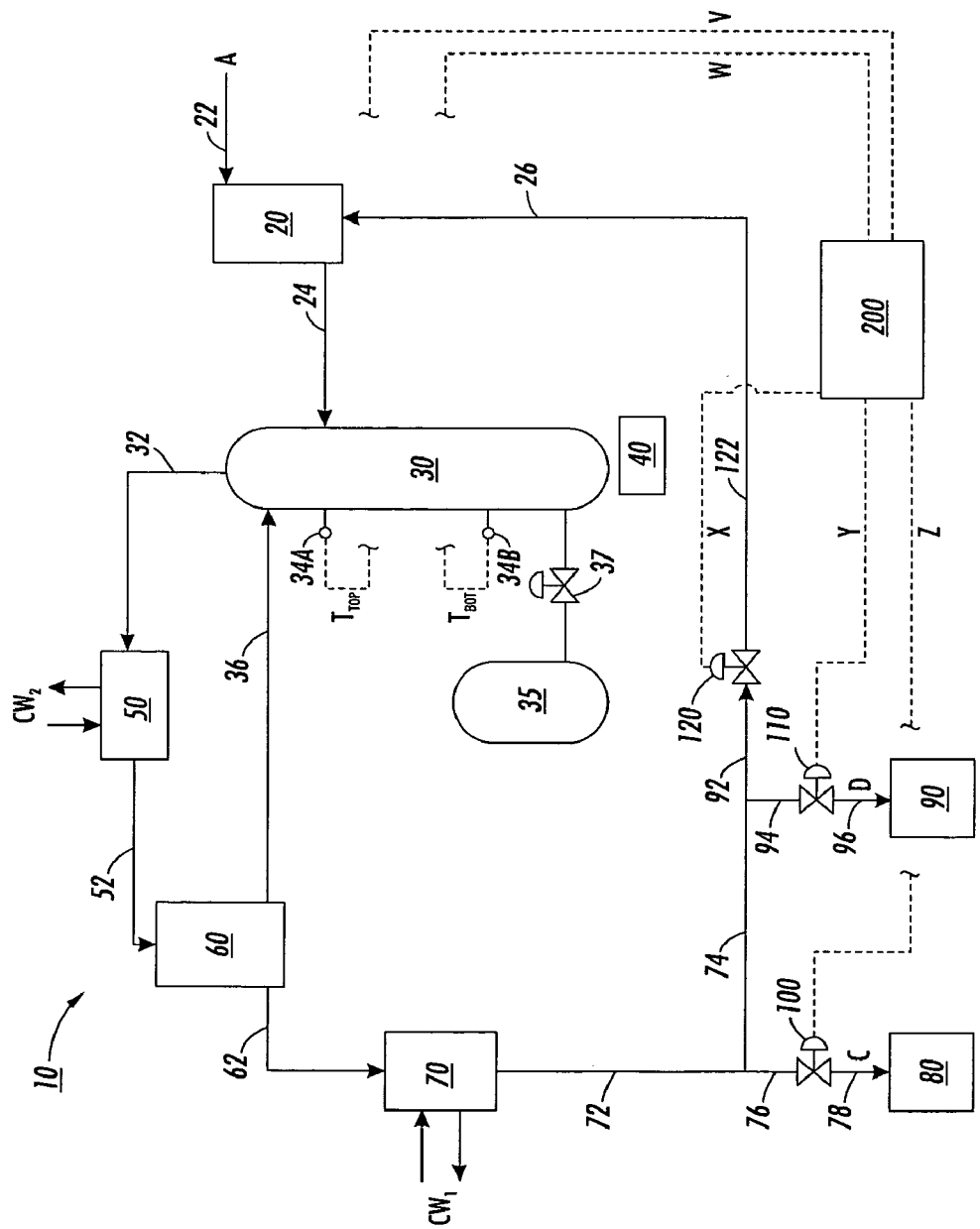
FIG. 1 is a process schematic according to the exemplary embodiment.

Conventional processes for reclaiming methylene chloride often result in disposing below grade or off-specification methylene chloride of relatively high purity but not reagent grade (99.99%). The present exemplary embodiment utilizes a "recycle" immediately following the reagent grade methylene chloride cutoff point. This purge aspect redirects the below grade or off-specification methylene chloride back to the system feed tank rather than being disposed. By doing this, the off-specification methylene chloride is recycled in each batch thereby enabling increased reclaim efficiency of methylene chloride at reagent grade purity.

In a typical photoreceptor fabrication process, following an AMAT coating process, solvent laden air is purified through one or more carbon adsorbers. The absorber purifies the solvent laden air produced during the coating process. The absorber is then regenerated by steam produced by a steam generator, the steam is pumped through the carbon thereby capturing the solvents by the carbon particles. The steam/solvents mixture is then condensed. The condensed water/solvent mixture produced alone can be directed to a batch distillation process which boils the water/solvent mixture. The solvents boiling at a lower temperature than water are driven out of the boiler section and in the form of vapor rise up the distillation column. In this vapor form, they are refined and purified as they reach the upper levels of the column. These vapors finally exit the top of the column where they are condensed. The condensed liquid then flows through a reflux divider where the flow is split, with a portion being returned to the top of the column where it is revaporized and assists in refining the vapors at that point in the column. The remaining liquid is passed through a product cooler and either stored as pure methylene chloride or directed to a flammable waste tank for future disposal.

The present exemplary embodiment relates to the addition of a recycle operation. During the "product cut" or reclamation of pure methylene chloride, a control system monitors the top column temperature and the temperature of the "bottoms" or lower region of the distillation column. The term "bottoms" as used herein refers to the portion of the distillation column, generally located in a lower region of the column, at which the operating temperatures are typically the highest. When the top temperature reaches 101.5° F. and the bottom temperature reaches 104.5° F., the quality, i.e. concentration, of the methylene chloride cut begins to drop below the reagent grade level. At this point the recycle is initiated by causing the product valves to switch to the batch column feed tank rather than the flammable waste tank. The recycle remains active so long as the top temperature is greater than or equal to 102° F. and the bottom temperature is greater than or equal to 125° F. The recycle is terminated upon either or both of the top temperature being less than 102° F. and/or the bottom temperature being less than 125° F. At this point the solvent concentration of methylene chloride has dropped to less than 25%. The recycle is then terminated by causing the product valves to switch to the flammable waste tank. The distillation process continues until the top column temperature reaches 212° F. indicating that all the solvents have been removed with only water remaining. The water is then pumped to the steam generator feed tank and reused to make steam for adsorber regeneration.

The exemplary process schematic is illustrated in FIG. 1. The system 10 comprises a feed tank 20 which receives waste stream A. The waste stream A can be a waste stream from a photoreceptor fabrication process. The waste stream A contains water and methylene chloride, and potentially additional solvents. The system 10 also includes a distillation unit 30 and a heat source 40. A steam generator 35 can be provided as the heat source 40. The heat input to the unit 30 from the generator 35 may be governed by a control valve 37. A temperature sensor 34 A is provided at the top region of the distillation unit 30. A temperature sensor 34B is provided at the bottom region of the distillation unit 30. The system 10 also comprises heat exchangers 50 and 70 and one or more sources of a cooling medium such as cooling water designated in FIG. 1 as $CW_1$ and $CW_2$. The system 10 additionally comprises a reflux divider 60. And, the system 10 comprises a product tank 80 for storing reclaimed methylene chloride, i.e., shown as stream C. The system 10 also comprises a waste tank 90 for collecting minor waste stream D. System 10 also includes valves 100, 110, and 120 and associated flow lines as further described below.

The operation of system 10 is as follows. Waste stream A containing water, methylene chloride and potentially additional solvents is directed through a flow line 22 to the feed tank 20. The contents of the feed tank 20 are fed to the distillation unit 30 through feed line 24. As will be understood by those skilled in the art, heat from the heater 40, or steam from the generator 35, vaporizes components in the feed into a vapor component which exits the distillation unit through flow line 32. The sensor 34A measures the temperature of the exiting vapor. That temperature information is designated as $T_{TOP}$. The sensor 34B measures the temperature of the column bottoms, designated as $T_{BOT}$. Flowing vapor from line 32 enters the heat exchanger 50 which induces full or partial condensation of the vapor. A supply of cooling water $CW_2$ is used. The cooled methylene chloride rich stream flows through line 52 into the reflux divider 60, which forms two exiting streams. A first stream is returned to the distillation unit 30 through the line 36, and the second stream is directed through flow line 62 to the second heat exchanger 70. Cooling water $CW_1$ is utilized to reduce the temperature of the methylene chloride rich stream. Flow lines 72, 74, 76, 78, 92, 94, and 96 provide flow communication from the outlet of the heat exchanger 70 to one or more of the product tank 80, waste tank 90, and the valve 120 as shown. Flow lines 26 and 122 provide flow communication between valve 120 and the feed tank 20.

Depending upon the temperature $T_{TOP}$ and $T_{BOT}$ detected by the temperature sensors 34A and 34B, a controller 200 positions each of the valves 100, 110 and 120 as described herein. The controller 200 is in communication with the temperature sensors 34A and 34B via lines W and V, and in further communication with each of valves 100, 110 and 120 via lines Z, Y and X, respectively. It will be appreciated that each of lines V, W, X, Y, and Z are electrical communication or signal lines. And the respective valves can be positioned by actuating assemblies known in the art.

During operation of the system 10, the methylene chloride-rich product stream is directed to the product tank 80 if the temperature measured by sensor 34A, i.e., $T_{TOP}$, is less than or equal to 101.5° F. and/or if the temperature measured by sensor 34B, i.e., $T_{BOT}$, is less than 104.5° F. During this phase of the process, the controller 200 receives control signals from the temperature sensors 34A and 34B and opens valve 100 and closes, or confirms closure of valves 110 and 120.

When the temperature measured by sensor 34A, i.e. $T_{TOP}$, is greater than 101.5±0.3° F., preferably 101.5° F., and the temperature measured by sensor 34B, i.e., $T_{BOT}$, is greater than or equal to 104.5±0.5° F., preferably 104.5° F., controller 200 opens valve 120 and closes, or confirms closure of, valves 100 and 110. This initiates the recycle operation. It will be appreciated that if a different temperature value is used than the preferred values, e.g., 101.3° F. for $T_{TOP}$, appropriate modification of the operating cycle is made. In such an example, the product stream would be directed to the product tank 80 so long as the temperature measured by sensor 34A is less than or equal to 101.3° F.

The recycle operation is continued so long as the temperature measured by sensor 34A, i.e., $T_{TOP}$, is greater than or equal to 102±0.3° F., preferably 102° F., and the temperature measured by sensor 34B, i.e. $T_{BOT}$, is greater than or equal to 125±5.0° F., preferably 125° F. If either of these conditions is not met, or if both of these conditions are not met, then the controller 200 terminates the recycle operation and closes valve 120 and opens valve 110 so that the product stream is directed to the waste tank 90. Valve 100 remains closed.

30 if a critical minimal level is reached within the distillation unit, such as, for example about 30% of its capacity. Furthermore, the various process units, components, and hardware and sources therefore will be understood by those skilled in the art.

The advantages of the present exemplary embodiment are financial and environmental. By increasing the efficiency of methylene chloride reclamation, the purchase and thus cost of methylene chloride is significantly reduced. Furthermore, the amount of hazardous waste generated is also significantly reduced.

In this regard, batch column testing was conducted to estimate savings from use of the present discovery exemplary embodiment. The following quantities of reclaimed methylene chloride were produced as shown in Table 2:

TABLE 2

Amounts of Methylene Chloride Typically Reclaimed

| | |
|---|---|
| Month 1 | 2436 gal |
| Month 2 | 2154 gal |
| Month 3 | 1429 gal |
| | 6019 Gals/qtr |
| | 68617 Lbs/qtr |
| | 68564 Reclaimed Lbs/qtr |
| | 24076 Est Annual Gallons |
| | 274254 Est Annual Lbs |

These amounts of reclaimed methylene chloride result in a substantial cost savings. Additionally, the purity of the reclaimed methylene chloride was exceedingly high. The following data set forth in Table 3 was obtained illustrating the batch column operating characteristics using the recycle as described herein:

TABLE 3

Batch Column Testing

| Time | Temp Top | Temp Mid | Temp Bottom | Temp Tank | Vis % H$_2$O | Ethanol | Vinyl Chloride | CLORO | THF | CYCLENE | HEP | TOL | CYCLE ONE |
|---|---|---|---|---|---|---|---|---|---|---|---|---|---|
| 13:43 | 100.3 | 101.1 | 111.5 | 150.2 | 0% | 424 | 0 | 0 | 57 | 2 | 98 | 36 | 2 |
| 13:45 | 100.2 | 101.1 | 113.5 | 155.0 | 0% | 509 | 0 | 0 | 6 | 3 | 134 | 1 | 0 |
| 13:49 | 100.3 | 101.1 | 114.7 | 160.0 | 0% | 518 | 0 | 0 | 3 | 3 | 145 | 0 | 0 |
| 13:53 | 100.3 | 100.9 | 118.3 | 165.0 | 0% | 541 | 0 | 0 | 6 | 4 | 205 | 0 | 0 |
| 13:57 | 100.2 | 101.2 | 122.8 | 170.0 | 0% | 634 | 0 | 0 | 11 | 10 | 465 | 0 | 0 |

It will be appreciated that the present exemplary embodiment system can utilize a wide array of process components. For example, instead of using multiple control valves, a single valving unit that provides a plurality of outputs may be employed. And, it will be appreciated that various sensor and signal configurations can be used. For example, a single control signal could be utilized for providing communication between the two temperature sensors 34A and 34B, and the controller 200. Additionally, it may be desired in certain embodiments to limit the maximum thermal energy input to the distillation unit 30 to about 55% during the recycle operation. A further safety limit may be implemented by configuring the controller 200 to close the steam valve 37 upon sensing that the pressure of the entering steam exceeds 75% of its maximum pressure. Appropriate pressure sensors on the distillation unit 30 would be used, in communication with the controller 200. A further safety measure that may be implemented is to terminate operation of the distillation unit The present exemplary embodiment diverts technical grade solvent back into feed tank or feed stream where it undergoes a subsequent pass through the distillation unit, capturing a significant fraction of the previously unclaimed methylene chloride. In a typical photoreceptor fabrication process, the exemplary embodiment will save a substantial amount of methylene chloride per year. EPA regulations require businesses to install the most efficient solvent recovery system available so this process has potential commercial value.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A process for improving the reclaim efficiency of methylene chloride from a mixture including water and methylene chloride, said process comprising:

providing a system including (i) a distillation unit having an inlet and an outlet, (ii) a plurality of selectively positionable control valves, each having an inlet and an outlet, one of said outlets being in communication with said inlet of said distillation unit, (iii) a plurality of temperature sensors and means for providing a control signal corresponding to sensed temperatures, and (iv) a controller in communication with said temperature sensors and said control valves;

directing said mixture including water and methylene chloride to said inlet of said distillation unit;

operating said distillation unit to produce a product stream at said outlet of said distillation unit;

measuring the temperature of said product stream and at a lower region of said distillation unit with said temperature sensors;

providing said control signal from said temperature sensors to said controller;

operating said controller to selectively position said control valves based upon said control signal;

whereby upon measuring the temperature of said product stream to be greater than 1.05° F. and the temperature at said lower region of said distillation unit to be greater than or equal to 104.5° F., said controller positions said control valves to direct said product stream to said inlet of said distillation unit.

2. The process of claim 1 further comprising:

maintaining directing of said product stream to said inlet of said distillation unit so long as the temperature of said product stream is greater than or equal to 102° F. and the temperature at said lower region of said distillation unit is greater than or equal to 125° F.

3. The process of claim 2 wherein when the temperature of said product stream falls below 102° F., or the temperature at said lower region of said distillation unit falls below 125° F., said controller positions said control valves to direct said product stream to a waste tank.

* * * * *